United States Patent
Garner et al.

(10) Patent No.: US 9,789,119 B2
(45) Date of Patent: *Oct. 17, 2017

(54) COGNITIVE FUNCTION

(71) Applicant: The Board of Trustees of the Leland Stanford Junior University, Palo Alto, CA (US)

(72) Inventors: Craig C. Garner, Los Altos, CA (US); H Craig Heller, Stanford, CA (US); Damien Colas, Stanford, CA (US); Daniel Z. Wetmore, San Francisco, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 14/610,976

(22) Filed: Jan. 30, 2015

(65) Prior Publication Data

US 2015/0246054 A1 Sep. 3, 2015

Related U.S. Application Data

(63) Continuation of application No. 13/327,226, filed on Dec. 15, 2011, now Pat. No. 8,946,206.

(60) Provisional application No. 61/424,168, filed on Dec. 17, 2010.

(51) Int. Cl.
*A61K 31/55* (2006.01)
*A61K 31/365* (2006.01)
*A61K 36/16* (2006.01)

(52) U.S. Cl.
CPC ............ *A61K 31/55* (2013.01); *A61K 31/365* (2013.01); *A61K 36/16* (2013.01)

(58) Field of Classification Search
CPC ....... A61K 36/16; A61K 31/365; A61K 31/55
See application file for complete search history.

(56) References Cited

U.S. PATENT DOCUMENTS

| | | | |
|---|---|---|---|
| 6,277,838 B1 | 8/2001 | Upasani et al. | |
| 6,399,604 B1 | 6/2002 | Albaugh et al. | |
| 6,426,343 B1 | 7/2002 | Dawson | |
| 8,729,067 B2 * | 5/2014 | Garner | A61K 31/34 514/214.02 |
| 8,946,206 B2 * | 2/2015 | Garner | A61K 31/55 514/214.02 |
| 2003/0092912 A1 | 5/2003 | DeSimone et al. | |
| 2008/0009475 A1 | 1/2008 | Garner et al. | |
| 2009/0270373 A1 | 10/2009 | Rao et al. | |
| 2010/0029770 A1 | 2/2010 | Roberts et al. | |
| 2014/0296210 A1 * | 10/2014 | Garner | A61K 31/34 514/214.02 |

FOREIGN PATENT DOCUMENTS

| | | |
|---|---|---|
| WO | WO 99/43661 A2 | 9/1999 |
| WO | WO 03/013514 A1 | 2/2003 |

OTHER PUBLICATIONS

Buckley et al. Jul. 2007, vol. 12, Issue 1, pp. 20-21.*
Rueda et al. 2008, Neuroscience Letters, vol. 433, pp. 22-27.*
Arai et al., "Excessive glutamate receptor 1 immunoreactivity in adult Down syndrome brains," Pediatr. Neurol. (1996) vol. 15, No. 3, pp. 203-206.
Atack et al., Neuropharmacology (2006) vol. 51, No. 6, pp. 1023-1029.
Bauer, "Twenty-four hour proactive facilitation of avoidance and discrimination by pentylenetetrazol," Psycopharmacologia (Berl.) (1972) vol. 24, pp. 275-295.
Belichenko et al., "Synaptic structural abnormalities in the Ts65Dn mouse model of Down Syndrome," J. Comp. Neruol. (2004) vol. 480, No. 3, pp. 281-298.
Berman et al., "Pentylenetetrazol (metrazol) in mental deficiency," AMA J. Dis. Child. (1957)vol. 94, No. 3, pp. 231-233.
Bumbalo et al., "Treatment of Down's Syndrome with the 'U' series of drugs," JAMA (1964) vol. 187, No. 5, p. 361.
Colas et al., Sleep, 2010, vol. 33, Abst 0098, p. A36 (24th Annual Meeting of the Associated Professional Sleep Societies, LLC, San Antonio TX, Jun. 5-9, 2010.
Donfrancesco and Dell'Uomo, "Ginkgo biloba in Down Syndrome," Phytomedicine (2004) vol. 11, No. 6, p. 469.
Fernandez et al., "Pharmacotherapy for cognitive impairment in a mouse model of Down syndrome," Nature Neuroscience (2007) vol. 10, pp. 411-413.
Gross et al., "Oral metrazol therapy in psychotic senile and arteriosclerotic patients," J. Am. Geriatr. Soc. (1954) vol. 2, No. 8, pp. 514-518.
Hamm et al., Society of Neuroscience Abstracts, 24th Annual Meeting of the Society for Neuroscience (1994) vol. 20, No. 1-2, p. 193, Abstract # 84.14.

(Continued)

*Primary Examiner* — Kara R McMillian (57) ABSTRACT

Provided herein are methods, drug formulations, and dosing regimens for improving cognitive function in a normal or cognitively impaired subject. For instance, methods provided herein comprise administering a $GABA_A$ receptor antagonist so that peak concentration of the $GABA_A$ receptor antagonist occurs when the subject is asleep.

11 Claims, 1 Drawing Sheet

(56) References Cited

OTHER PUBLICATIONS

Heller et al., Lecture Notes in Computer Science, Foundations of Augmented Cognition (2009) vol. 5638, pp. 818-825, Springer Publishing.
Ivic et al., "Terpene trilactones from Ginkgo biloba are antagonists of cortical glycine and GABA(A) receptors," J. Biol. Chem. (2003) vol. 278, No. 49, pp. 49279-49285.
Krivanek et al., "Effects of pentylenetetrazole on memory storage in mice," Psychopharmacologia (1968) vol. 12, No. 4, pp. 303-321.
Lieberman et al., "Subconvulsive intravenous metrazol therapy in mental patients; a preliminary report," Geriatrics (1954) vol. 9, No. 3, pp. 125-127.
Lieberman et al., "Evaluation of Intravenous and Oral Use of Metrazol in Hospitalized Arteriosclerotic Psychiatric Patients," Geriatrics (1954) vol. 9, No. 8, pp. 371-374.
Lu et al., "A controlled study of drugs in long-term geriatric psychiatric patients," Arch. Gen. Psychiat. (1971) vol. 25, pp. 284-288.
Ruby et al., "Circadian locomotor rhythms are normal in Ts65Dn "down syndrome" mice and unaffected by pentylenetetrazole," J Biol Rhythms (2010) vol. 25, pp. 63-66.
Solomon et al., "Ginkgo for memory enhancement: a randomized controlled trial," JAMA (2002) vol. 288, No. 7, pp. 835-840.
Turkel et al., "Medical amelioration of Down's Syndrome incorporating the orthomolecular approach," Orthomolecular Psychiatry (1975) vol. 4, No. 2, pp. 102-115.
Varvel et al., "Delta(9)-THC-induced cognitive deficits in mice are reversed by the GABA(A) antagonist bicuculline," Psychopharmacology (2005) vol. 178, No. 2-3, pp. 317-327.

* cited by examiner

Figure 1

COGNITIVE FUNCTION

1. CROSS-REFERENCE TO RELATED APPLICATION

This application is a continuation of U.S. application Ser. No. 13/327,226, filed Dec. 15, 2011, which claims the benefit of U.S. provisional application No. 61/424,168, filed Dec. 17, 2010, each of which is incorporated herein by reference in its entirety.

2. FIELD OF THE INVENTION

Provided herein are methods for improving cognitive function by administration of, e.g., a $GABA_A$ receptor antagonist, as well as formulations and dosing regimens useful for improving cognitive function, and so relates to the fields including those of molecular biology, pharmacology, and medicine.

3. BACKGROUND

Cognitive impairment can reduce the capacity of individuals to learn, remember, communicate, socialize, problem solve, and/or function independently. It may be due to a neurodevelopmental or neurodegenerative disorder caused by genetic and/or environmental factors, or it may be an acquired condition.

Neurodevelopmental disorders that manifest themselves in cognitive impairment include, for example, Down syndrome, phenylketonuria, neurofibromatosis type 1, maple syrup urine disease, fetal alcohol syndrome, Rett syndrome, neonatal malnutrition, fragile X syndrome, and autism spectrum disorders. Neurodevelopmental disorders affect 2-3% of the population in the industrialized world. The most common neurodevelopmental disorder with a known genetic etiology is Down syndrome, which occurs in approximately 1/700-1,000 live births, and is caused by total or partial triplication of chromosome 21 (Hsa21), resulting in the overexpression of approximately 300-400 genes.

Neurodegenerative disorders that manifest themselves in cognitive impairment include, for example, Parkinson's disease, Huntington's disease, vascular dementia, idiopathic dementia, and Alzheimer's disease. Alzheimer's disease alone affects more than 25 million people worldwide and more than 5 million Americans, and is the $7^{th}$ leading cause of death in the United States. The risk of developing a neurodegenerative disorder generally increases with age.

In addition to cognitive impairment caused by neurodevelopmental or neurodegenerative disorders, acquired conditions may also impair cognitive function in normal subjects. Such acquired conditions include "jet" lag, circadian rhythm disruptions, sleep apnea, and sleep disturbances.

Cognitive function is generated by neuronal networks that exhibit an appropriate balance of inhibition and excitation. Although excitation is the primary way of information transfer between various brain regions, inhibition plays an equally important role in many neuronal networks by being responsible, for example, for bursting and oscillatory activity. Imbalanced excitation and inhibition in neuronal networks can result in reduced brain function and/or pathology. For example, excessive excitation can produce epilepsy or seizures, and excessive inhibition can lead to cognitive deficits or sedation.

A major inhibitory neurotransmitter in the mammalian central nervous system is γ-aminobutyric acid (GABA). One of the receptors for GABA signaling in the mammalian central nervous system is the $GABA_A$ receptor, which is a heteropentameric, ligand-gated anion channel. Binding of GABA to the $GABA_A$ receptor results in increased influx of chloride ions across the post-synaptic membrane. Such increased chloride ion conductance produces inhibition of depolarization, or even hyperpolarization, of the post-synaptic membrane, and thus an inhibition of neuronal firing of the postsynaptic neuron.

Excessive inhibition mediated by the $GABA_A$ receptor has been documented in a mouse model of Down syndrome, namely in the Ts65Dn mouse. The Ts65Dn mouse is trisomic for about 100 genes on mouse chromosome 16 (Mmu16) that are homologous to genes on Hsa21 in human Down syndrome patients. Ts65Dn mice exhibit learning and memory deficits and corresponding anatomical and physiological abnormalities that are similar to those found in human Down syndrome patients. Interestingly, in the hippocampus of Ts65Dn mice excessive activity of inhibitory neurons has been shown, concomitant with deficits in hippocampal long-term potentiation (LTP) induction.

Interestingly, hippocampal LTP induction and cognitive function in Ts65Dn mice has been shown to improve in a long-lasting manner by the short-term administration of low doses of compounds such as pentylenetetrazole (PTZ), bilobalide (BB), and picrotoxin (PTX) that reduce inhibition mediated by the $GABA_A$ receptor. See, e.g., Fernandez et al., 2007, *Nat. Neurosci.* 10: 411-3; Rueda et al., 2008, *Neurosci. Lett.* 433: 22-7; Costa & Grybko, 2005, *Neurosci. Lett.* 382: 317-22; Kleschevnikov et al., 2004, *J. Neurosci.* 24: 8153-60; U.S. Patent App. Pub. No. 2008/0009475.

Numerous diseases exhibit circadian variation in progression, symptoms, and risk. The chronobiology of symptom severity has been confirmed for hypertension, cardiovascular disease (heart attack), stroke, arthritis, asthma, gastrointestinal disorders, epilepsy, multiple sclerosis, and other disorders. Circadian rhythm sensitive dosing aims to target drugs to the portions of the circadian cycle during which disease progression, symptoms, risk, or treatment efficacy are highest. No such chronotherapeutic strategy for cognitive impairment has been described.

Proper memory function requires encoding a memory during learning, consolidation of that recently acquired memory to long-term memory in the hours and days that follow, and retrieval of the learned content. Consolidation of memories occurs primarily during sleep. See, e.g., Stickgold, 2005, *Nature* 437(7063): 1272-8. Sleep is composed of a repeating cycle of phases that can be identified by differences in the brain and body, including variation in brain rhythms, heart rate, and movement. The sleep cycle includes rapid eye movement (REM) sleep and non-REM sleep that is divided into light sleep and deep sleep. Deep or 'slow-wave' sleep (SWS) is important for consolidating long-term memories. See, e.g., Diekelmann and Born, 2010, *Nat. Rev. Neurosci.* 11(2): 114-26). During the course of a period of sleep—for instance a night of sleep in a human—the proportion of time spent in the various phases of sleep generally changes. In particular, REM portions of the cycle become longer and non-REM portions of the cycle become shorter during the course of a night of sleep.

Recent discoveries in the fields of neurobiology, psychology, and sleep research have characterized the important relationship between sleep and memory. Sleep is required for normal memory consolidation and the amount of high-quality sleep can impact the level of cognitive function. In people, intensive periods of learning cause an increase in the amount of SWS the following night. See Eschenko et al., 2008, *Learn. Mem.* 15(4): 222-8. This suggests that SWS is required for memories to be consolidated. See Ellenbogen et al, 2006, *Curr. Opin. Neurobiol.* 16(6): 716-22. In rodents, patterns of activity of neurons in the hippocampus, a key brain region for memory, occur in a predictable and sequential pattern when a rodent explores a maze or other environment. See, e.g., Davidson et al., 2009, *Neuron* 63(4): 497-507; Wilson and McNaughton, 1994, *Science* 265 (5172): 676-9; Wilson and McNaughton, 1993, *Science* 261(5124): 1055-8. The spatial memory represented by this experience is thought to be consolidated during sleep. Electrical recordings of neuronal activity during SWS have identified the 'replay' of patterns of neural activity observed during previous experience. See, e.g., Euston et al., 2007, *Science* 318(5853): 1147-50; Ji and Wilson, 2007, *Nat. Neurosci.* 10(1): 100-7; Lee and Wilson, 2002, *Neuron* 36(6): 1183-94; Louie and Wilson. 2001, *Neuron* 29(1): 145-56; Shen et al., 1998, *J. Sleep Res.* 7(Suppl 1): 6-16. This suggests that replay is an important mechanism for memory consolidation. Interrupting replay during sleep disrupts memory formation. See Ego-Stengel and Wilson, 2010, *Hippocampus* 20(1): 1-10.

Current drug therapies for cognitive impairment are at best symptomatic and supportive therapies. Consequently, there is an unmet medical need for drugs and methods for treating or preventing cognitive deficits, a need that is steadily increasing in our ageing Western civilization. Such treatments might also benefit normal individuals in improving cognitive functions.

4. SUMMARY OF THE INVENTION

Provided herein are methods for improving the cognitive function in normal or cognitively impaired subjects. In some embodiments, a subject is administered an effective dose of a $GABA_A$ receptor antagonist while the subject is sleeping, over a period of time (e.g., a number of days or weeks) sufficient to improve cognitive function. In certain embodiments, a subject is administered an effective dose of a $GABA_A$ receptor antagonist such that peak concentrations of the $GABA_A$ receptor antagonist in the brain of the subject are achieved during sleep of the subject, for a period of time sufficient to improve cognitive function in the subject. In some embodiments, the $GABA_A$ receptor antagonist is, for example, pentylenetetrazole (PTZ). The methods can provide long-term cognitive improvement that can persist after cessation of treatment. The methods may be applied to the treatment or prevention of a variety of cognitive impairment conditions, including Down syndrome and Alzheimer's disease, and of acquired conditions including "jet" lag and circadian rhythm disruption, as well as to the improvement of cognitive function in normal subjects.

In certain aspects, formulations and dosing regimens are provided herein useful for improving cognitive function.

5. BRIEF DESCRIPTION OF THE FIGURE

The present disclosure is best understood when read in conjunction with the accompanying figure, which serves to illustrate certain embodiments. It is understood, however, that the disclosure is not limited to the specific embodiments disclosed in the figure.

As seen in Panel A, chronic administration of PTZ dosed at 0.3 mg/kg during the middle of the dark cycle (wakefulness) is less effective in improving performance in the NOR task in Ts65Dn mice as compared to administering during the middle of the light cycle (sleep), as shown in Panel B. Chronic administration of PTZ dosed at 0.3 mg/kg during the middle of the light cycle (sleep) normalizes performance in the Novel Object Recognition (NOR) task in Ts65Dn mice.

6. DETAILED DESCRIPTION OF THE INVENTION

6.1. Definitions

The following terms used herein shall have the meanings as indicated below.

The term "$GABA_A$ receptor antagonist", as used herein, refers to a compound that inhibits the activity of the $GABA_A$ receptor, e.g., by reducing the influx of chloride ions through the pore of the $GABA_A$ receptor, and/or by blocking or reducing binding of an agonist to the $GABA_A$ receptor, and/or blocking or reducing an effect of an agonist on the $GABA_A$ receptor. In certain embodiments, a $GABA_A$ receptor antagonist can, for example, be a negative allosteric modulator, a non-competitive channel blocker or an inverse agonist. Exemplary $GABA_A$ receptor antagonists include bicuculline, bilobalide (BB), cicutoxin, ginkgolide B, pentylenetetrazole (PTZ), picrotoxin (PTX), 3-(5-methylisoxazol-3-yl)-6-[(1-methyl-1H-1,2,3-triazol-4-yl)methoxy][1,2,4]triazolo[3,4-a]phthalazine (α5IA), 3,10-dichloro-9H-benzo[f]imidazo[1,5-a][1,2,4]triazolo[1,5-d][1,4]diazepine (RO4882224), 3-bromo-10-difluoromethyl-9H-imidazo(1,5-a)(1,2,4)triazolo(1,5-d)(1,4)benzodiazepine (RO4938581), and RG1662, among others.

The term "subject", as used herein, refers to an animal, preferably a mammal, including mouse, rat, rabbit, dog, cat, guinea pig, goat, cow, horse, pig, sheep, monkey, primate, ape, and human. The term "normal subject", as used herein, refers to a subject that is not cognitively impaired as determined by a protocol for assessing cognitive function.

The term "cognitive function", as used herein, refers to a subject's ability to store and retrieve memories, learn, communicate, and/or function independently.

The term "cognitive impairment", as used herein, refers to i) a given subject's reduced capacity over time to store or retrieve memories, learn, communicate, or function independently and/or ii) a given subject's reduced capacity to store or retrieve memories, learn, communicate, or function independently, as compared to the capacities to store or to retrieve memories, learn, communicate, or function independently, of other appropriately matched subjects, e.g., subjects of a similar age to the given subject and/or not having a condition, such as jet lag, congenital disorder, etc., that afflicts the given subject.

The terms "therapeutic level," "therapeutically effective dose," "therapeutically effective amount," and the like, as used herein, refer to an amount or concentration of a compound or agent, e.g., a $GABA_A$ receptor antagonist, that achieves a therapeutic effect in a subject, wherein the therapeutic effect can be a) an amelioration or alleviation, if not complete cessation, of a cognitive impairment, including but not limited to a memory or learning disability; or b) prevention of such cognitive impairment. A "minimum therapeutic level", as used herein, refers to the minimum concentration of a compound required to achieve a therapeutic effect.

The term "active metabolite", as used herein, refers to a compound that is derived from another compound via in vivo metabolism, and that has therapeutic efficacy.

The term "sleep", as used herein, refers to the naturally recurring state of a subject characterized by reduced or absent consciousness, relatively suspended sensory activity, and inactivity of nearly all voluntary muscles.

The term "circadian cycle sensitive administration", as used herein, refers to the administration of a compound or agent, e.g., a $GABA_A$ receptor antagonist, to a subject such that a therapeutic level of the compound or agent, e.g., a $GABA_A$ receptor antagonist, is reached at a predetermined point during the subject's circadian cycle.

"Peak concentration", as used herein, refers to the maximum concentration of a compound or agent, e.g., a $GABA_A$ receptor antagonist, that occurs after being administered to a subject. In various embodiments, the peak concentration can, for example, be in the subject's blood, plasma, brain, cerebrospinal fluid, etc. A peak concentration can, for instance, be a $C_{max}$.

As used herein, the term "$T_{max}$" refers to the time to reach a peak concentration following administration of the compound or agent, e.g., a $GABA_A$ receptor antagonist, to the subject. Generally, as explained below, the $T_{max}$ should be such that the peak concentration of the compound or agent, e.g., a $GABA_A$ receptor antagonist, occurs during a subject's sleep period, which may be, for example, the early part of a subject's sleep period, the middle of a subject's sleep period or late part of the sleep period.

6.2. Improving Cognitive Function

In one aspect, provided herein are methods for improving cognitive function or preventing a reduction in cognitive function in normal or cognitively impaired subjects via circadian cycle sensitive administration of a compound that reduces inhibitory neuronal activity, e.g., $GABA_A$ receptor antagonist. Without intending to be limited by any theory or mechanism of action, it is demonstrated in the examples provided herein that doses of PTZ, a $GABA_A$ receptor antagonist, administered to Ts65Dn mice during a sleep cycle can improve cognition while the same doses of PTZ administered to Ts65Dn mice during a wake cycle were less effective in improving cognitive function. Thus, to achieve optimal therapeutic benefits, $GABA_A$ receptor antagonists such as PTZ, BB, and PTX, should be administered such that peak concentrations are achieved in the subject during the sleep cycle.

In one embodiment, the present disclosure provides methods for improving cognitive function or preventing a reduction in cognitive function in a subject by administering a compound that reduces inhibitory neuronal activity, e.g., $GABA_A$ receptor antagonist, so that therapeutic levels of the compound or of an active metabolite of the compound in the brain of the subject are achieved during the portion of the circadian cycle when the subject sleeps.

For example, a $GABA_A$ receptor antagonist can be administered during the sleep cycle of the treated subject.

In another embodiment, the $GABA_A$ receptor antagonist can be administered to subject in a form (e.g., delayed release or sustained release or other suitable form) that will result in a peak concentration occurring in the subject while the subject is asleep.

Circadian cycle sensitive dosing of compounds that reduce inhibitory neuronal activity, e.g., $GABA_A$ receptor antagonists, increases efficacy of improved cognitive function, and offers the potential for efficacy at lower doses to provide a larger therapeutic window relative to doses that cause side effects.

In some embodiments, the compound that reduces inhibitory neuronal activity is a $GABA_A$ receptor antagonist. In some embodiments, the $GABA_A$ receptor antagonist is a non-competitive inhibitor. In some embodiments, the $GABA_A$ receptor antagonist is a competitive inhibitor. In some embodiments, the $GABA_A$ receptor antagonist is an allosteric inhibitor. In some embodiments, the $GABA_A$ receptor antagonist is a non-selective $GABA_A$ receptor antagonist. In other embodiments, the $GABA_A$ receptor antagonist is a selective $GABA_A$ receptor antagonist. In yet other embodiments, the $GABA_A$ receptor antagonist is a channel blocker of the $GABA_A$ receptor. In some embodiments, the compound is selected from the group consisting of pentylenetetrazole (PTZ), bilobalide (BB), picrotoxin (PTX), ginkgolide B, 3,10-dichloro-9H-benzo[f]imidazo[1,5-a][1,2,4]triazolo[1,5-d][1,4]diazepine) (RO4882224), 3-bromo-10-difluoromethyl-9H-imidazo(1,5-a)(1,2,4)triazolo(1,5-d)(1,4)benzodiazepine (RO4938581), RG1662 and compound α5IA.

The methods provided herein may result in a partial or in a complete removal of a cognitive impairment, such as, for example, partial or complete removal of a memory or learning disability. For instance, the amount of improvement can be at least about 1.5-fold, at least about 2-fold, at least about 3-fold, at least about 5-fold, at least about 10-fold, at least about 15-fold, at least about 20-fold, at least about 25-fold, at least about 50-fold, at least about 75-fold, or at least about 100-fold as compared to a suitable control, e.g., an otherwise substantially identical subject (i.e., a subject having a similar deficit in cognitive ability) not administered a compound as provided herein, or the same subject prior to administration of the compound. In some embodiments, the improvement in cognitive function can be at least about 1%, about 2%, about 3%, about 4%, about 5%, about 6%, about 7%, about 8%, about 9%, about 10%, about 12%, about 15%, about 20%, about 25%, about 30%, about 40%, about 50%, about 60%, about 70%, about 80%, about 90%, about 100%, or greater.

In other embodiments, the methods provided herein may prevent the development or worsening of a cognitive impairment, such as, for example, prevention of development or worsening of a memory or learning disability. For instance, the methods provided herein may result in a delay of onset of a cognitive impairment of at least about 1 month, at least about 3 months, at least about 6 months, at least about 9 months, at least about 1 year, at least about 2 years, at least about 3 years, at least about 5 years, at least about 10 years, at least about 15 years, at least about 20 years, at least about 25 years, at least about 30 years, at least about 50 years, at least about 75 years, or more as compared to a suitable control, e.g., an otherwise substantially identical subject (i.e., a subject having a similar deficit in cognitive ability) not administered a compound as provided herein, or the same subject prior to administration of the compound. In some embodiments, the methods provided herein may prevent worsening of cognitive impairment, or may delay such worsening by at least about 1 month, at least about 3 months, at least about 6 months, at least about 9 months, at least about 1 year, at least about 2 years, at least about 3 years, at least about 5 years, at least about 10 years, at least about 15 years, at least about 20 years, at least about 25 years, at least about 30 years, at least about 50 years, at least about 75 years.

6.3 Subjects

In addition to the definition of "subject" provided above, it will be understood that the subject typically has a circadian cycle to her, his or its biological, physiological or behavioral processes. For instance, the subject may be nocturnal (i.e., active during the night and asleep during the day) or diurnal (i.e., active during the day and asleep during the night). The subject may be of any age, and may include adults and children. Children (e.g., neonates, infants, young children, adolescents) in particular may benefit from methods provided herein that improve cognitive function to a degree that would not occur in the absence of the treatment. In certain embodiments, the methods provided herein prevent the onset or the worsening of cognitive impairment. Children and adults that may benefit from methods provided herein may be identified by genetic testing for predisposition, e.g. by chromosome typing, by family history, or by other medical means.

In some embodiments, the subject does not have a measurable cognitive impairment or is not cognitively impaired.

In certain embodiments, the subject has a predisposition of developing a cognitive impairment. In some embodiments, the subject carries genetic markers of such predisposition, such as, for example, a triplication of chromosome 21 (Hsa21). In other such embodiments, the subject is otherwise thought to likely develop a cognitive impairment, e.g., due to impending "jet" lag, circadian rhythm disruption, sleep deprivation, or sleep disturbance.

In other embodiments, the subject has a cognitive impairment. Cognitive impairment reduces the capacity for a subject to store and retrieve memories, learn, communicate, and function independently. The cognitive impairment may be due to a neurodevelopmental or neurodegenerative disorder caused by genetic and/or environmental factors, or it may be an acquired condition. Examples of neurodevelopmental disorders that manifest themselves in cognitive impairment include but are not limited to Down syndrome, phenylketonuria, neurofibromatosis type 1, maple syrup urine disease, fetal alcohol syndrome, neonatal malnutrition, fragile X syndrome, Rett syndrome, and autism spectrum disorders. Examples of neurodegenerative disorders that manifest themselves in cognitive impairment include but are not limited to Parkinson's disease, Huntington's disease, vascular dementia, idiopathic dementia, and Alzheimer's disease. Examples of acquired conditions include but are not limited to "jet" lag, circadian rhythm disruptions, sleep apnea, and sleep disturbances.

In some embodiments, the subject has a cognitive impairment with a pattern of persistently slow learning of motor skills or language skills during childhood. In other embodiments, the subject develops a cognitive impairment with progressing age with a pattern of decreasing memory retention or memory recall skills. In some embodiments, the subject has a significantly below-normal global intellectual capacity as a child and/or as an adult. In some embodiments, the subject has a tested intelligence quotient (IQ) of 70 or below.

6.4 Compounds that Reduce Inhibitory Neuronal Activity

Compounds that reduce inhibitory neuronal activity for use in the methods provided herein include but are not limited to $GABA_A$ receptor antagonists. In certain embodiments, such compound is orally active, and can cross the blood brain barrier.

Without intending to be limited to any theory or mechanism, $GABA_A$ receptor antagonists may have a mechanism of action selected from the group consisting of: 1) blocking the $GABA_A$ receptor chloride ionophore (non-competitive inhibitors); 2) binding to the GABA binding site of the $GABA_A$ receptor, and thus reducing or eliminating binding of GABA and chloride conductance (competitive inhibitors); 3) binding to an allosteric site of the $GABA_A$ receptor, and thus reducing or eliminating GABA induced chloride conductance (functional allosteric inhibitors); and 4) binding to an allosteric site of the $GABA_A$ receptor, and thus reducing or eliminating binding of an allosteric inducer of chloride conductance (chemical allosteric inhibitors).

In some embodiments, the $GABA_A$ receptor antagonist is a non-competitive inhibitor. Non-competitive inhibitors of the $GABA_A$ receptor include but are not limited to pentylenetetrazole (PTZ), bilobalide (BB), picrotoxin (PTX), and ginkgolide B.

In other embodiments, the $GABA_A$ receptor antagonist is a competitive inhibitor. Competitive inhibitors of the $GABA_A$ receptor include but are not limited to bicuculline ((6R)-6-[(5S)-6-methyl-5,6,7,8-tetrahydro[1,3]dioxolo[4,5-g]isoquinolin-5-yl]furo[3,4-e][1,3]benzodioxol-8(6H)-one).

In yet other embodiments, the $GABA_A$ receptor antagonist is a functional or chemical allosteric inhibitor. The allosteric site of the $GABA_A$ receptor may be the benzodiazepine (BZD) binding site, which is located in the extracellular domain of the $GABA_A$ receptor at the interface of the α and γ subunits (Boileau et al. 2002 Neuropharmacology 43(4):695-700; Boileau et al. 1998 Mol Pharmacol 53(2):295-303; Sigel and Buhr 1997 Trends Pharmacol Sci 18(11):425-429), or another site that when bound by a ligand changes the conformation of the $GABA_A$ receptor and reduces its chloride ion conductance (functional allosteric inhibitors) or reduces binding of an allosteric inducer of chloride conductance (chemical allosteric inhibitors). Functional allosteric inhibitors that bind to the BZD binding site can, for example, be "inverse agonists". Functional and chemical allosteric inhibitors of the $GABA_A$ receptor include but are not limited to derivatives of imidazo[1,5-a][1,2,4]-triazolo[1,5-d][1,4]benzodiazepine (Knust et al. 2009 Bioorganic & Medicinal Chemistry Letters 19:5940-44), in particular compounds RO4882224 (3,10-dichloro-9H-benzo[f]imidazo[1,5-a][1,2,4]triazolo[1,5-d][1,4]diazepine) and RO4938581 (3-bromo-10-difluoromethyl-9H-imidazo(1,5-a)(1,2,4)triazolo(1,5-d)(1,4)benzodiazepine); α5IA (Dawson et al. 2006 J Pharmacol Exp Ther 316:1335-45); flumazenil (ethyl 12-fluoro-8-methyl-9-oxo-2,4,8-triazatricyclo[8.4.0.0$^{2,6}$]tetradeca-1(10),3,5,11,13-pentaene-5-carboxylate; also known as flumazepil or Ro 15-1788; active ingredient of ANEXATE, LANEXAT, MAZICON, or ROMAZICON); Ro15-3505 (sarmazenil; ethyl 7-chloro-5-methyl-6-oxo-5,6-dihydro-4H-imidazo[1,5-a][1,4]benzodiazepine-3-carboxylate); Ro15-4513 (ethyl-8-azido-5,6-dihydro-5-methyl-6-oxo-4H-imidazo-1,4-benzodiazepine-3-carboxylate); SR95531 (gabazine; 4-[6-imino-3-(4-methoxyphenyl)pyridazin-1-yl]butanoic acid hydrobromide); RY-023 (t-butyl 8-(trimethylsilyl) acetylene-5,6-dihydro-5-methyl-6-oxo-4H-imidazo[1,5a][1,4]benzodiazepine-3-carboxy-late); RY-80 (ethyl-8-acetylene-5,6-dihydro-5-methyl-6-oxo-4H-imidazo[1,5a][1,4]benzodiazepine-3-carboxylate); L-655,708 (ethyl (S)-11,12,13,13a-tetrahydro-7-methoxy-9-oxo-9H-imidazo[1,5-a]pyrrolo[2,1-c][1,4]benzodiazepine-1-carboxylate); certain benzothiophene derivatives (Chambers et al., 2003 J. Med. Chem. 46 (11):2227-40); certain triazolophthalazine derivatives (Sternfeld et al. 2004 J Med Chem. 47(9):2176-9; Street et al. 2004 J Med Chem. 47(14):3642-57); certain pyrazolotriazine derivatives (Chambers et al. 2004 J. Med. Chem. 47(24):5829-32); and RG1662, among others.

The heteropentameric $GABA_A$ receptors are formed in humans from 19 subunits. The subunits can be classified into α(1-6), β(1-3), γ(1-3), δ, ε, π and θ (1-3) subunit classes. Each $GABA_A$ receptor contains two α and two β subunits. The main subunit combination is the γ1α2β2 receptor, which accounts for about 40% of all $GABA_A$ receptors. $GABA_A$ receptor subtypes have distinct patterns of expression, biophysical properties, and pharmacology. For example, the α5 subtype constitutes only around 5% to 10% of total brain $GABA_A$ receptors; yet within the hippocampus, this subtype comprises around 25%. It can thus be expected that a $GABA_A$ receptor antagonist that has higher affinity and/or efficacy for the α5 subtype would exert its function primarily in certain areas of the brain or certain neurons and less in others, giving rise to specific effects. The specific effect may be deduced from the localization of particular subtypes of the $GABA_A$ receptor in the brain, or it may be determined experimentally.

In some embodiments, the $GABA_A$ receptor antagonist has comparable affinity and/or efficacy to each of the various subtypes of the $GABA_A$ receptor and thus produces quantitatively similar reductions of the inhibitory effects of GABA on the various subtypes of the $GABA_A$ receptor (non-selective $GABA_A$ receptor antagonist). In other embodiments, the $GABA_A$ receptor antagonist has different affinity and/or efficacy to the various subtypes of the $GABA_A$ receptor and thus produces quantitatively different reductions of the inhibitory effects of GABA on the various subtypes of the $GABA_A$ receptor (selective $GABA_A$ receptor antagonists). Such quantitatively different reductions of the inhibitory effects of GABA on the various subtypes of the $GABA_A$ receptor of a selective $GABA_A$ receptor antagonist may result in specific effects that include but are not limited to enhanced cognition and reduced anxiogenic and proconvulsant liabilities. Examples of compounds that have greater affinity and/or efficacy for the α5 subtype than for the α1, α2 or α3 subtypes include but are not limited to Ro 15-4513, L-655,708, RY-080 (Skolnick et al. 1997 *J Pharmacol Exp Ther* 283:488-93), PWZ-029 (8-chloro-3-(methoxymethyl)-5-methyl-4H-imidazo[1,5-a][1,4]benzodiazepin-6-one), RO4938581 (Ballard et al. 2009 *Psychopharmacology* 202: 207-23), α5IA (3-(5-methylisoxazol-3-yl)-6-[(1-methyl-1H-1,2,3-triazol-4-yl)methoxy][1,2,4]triazolo[3,4-a]phthalazine), NGD 97-1 (CP-457,920; Bednar et al. 2004 *Clin Pharmacol Ther* 75:P30), MRK-536 (Chambers et al. 2002 *J Med Chem* 45:1176-79; Chambers et al. 2003 *Med Chem* 46:2227-40; Atack et al. 2011 *Curr Top Med Chem* 11(9): 1203-14), MRK-016 (Chambers et al. 2004 *J Med Chem* 47:5829-32), RY-023, S-8510 ([2-(3-isoxazolyl)-3,6,7,9-tetrahydroimidazo[4, 5-d]pyrano[4,3-b]pyridine monophosphate monohydrate), RY-80, AC-3933 (5-(3-methoxyphenyl)-3-(5-methyl-1,2,4-oxadiazol-3-yl)-2-oxo-1,2-dihydro-1,6-naphthyridine), certain benzothiophene derivatives (Chambers et al., 2003 *J. Med. Chem.* 46 (11):2227-40), certain triazolophthalazine derivatives (Steinfeld et al. 2004 *J Med Chem.* 47(9):2176-9; Street et al. 2004 *J Med Chem.* 47(14):3642-57), certain pyrazolotriazine derivatives (Chambers et al. 2004 *J. Med. Chem.* 47(24):5829-32), and RG1662.

Compounds that reduce inhibitory neuronal activity suitable in the methods provided herein can be identified experimentally using a variety of in vitro and/or in vivo models. For example, $GABA_A$ receptors can be purified comprising various combinations of subunits, and compounds can be screened for binding to various sites of the purified receptor proteins. Compounds can also be functionally screened for their ability to inhibit a receptor involved in neuronal inhibition using in vitro culture systems. In addition, compounds can be evaluated as potential inhibitors of neuronal activity and for treatment or prevention of cognitive impairment using animal models (e.g., monkey, rat, or mouse models). In addition, the activity of a compound in kindling seizures or convulsions can be tested to enable selection of a compound that reduces inhibitory neuronal activity with a broad dosage difference between the desired effect of treating or preventing cognitive impairment, and the undesired effect of causing seizures. Candidate compounds that reduce inhibitory neuronal activity may also be identified by known pharmacology, structure analysis, or rational drug design using computer based modeling.

Candidate compounds that reduce inhibitory neuronal activity may encompass numerous chemical classes, though typically they are organic molecules, preferably small organic compounds having a molecular weight of more than 50 and less than about 2,500 daltons. They may comprise functional groups necessary for structural interaction with proteins (e.g., hydrogen bonding), and typically include at least an amine, carbonyl, hydroxyl, or carboxyl group. They often comprise cyclical carbon or heterocyclic structures and/or aromatic or polyaromatic structures substituted with one or more functional group. They may be found among biomolecules including peptides, saccharides, fatty acids, steroids, purines, and pyrimidines, and structural analogs thereof.

Candidate compounds that reduce inhibitory neuronal activity can be synthesized or isolated from natural sources (e.g., bacterial, fungal, plant, or animal extracts). The synthesized or isolated candidate compound s may be further chemically modified (e.g., acylated, alkylated, esterified, or amidified), or substituents may be added (e.g., aliphatic, alicyclic, aromatic, cyclic, substituted hydrocarbon, halo (especially chloro and fluoro), alkoxy, mercapto, alkylmercapto, nitro, nitroso, sulfoxy, sulfur, oxygen, nitrogen, pyridyl, furanyl, thiophenyl, or imidazolyl substituents) to produce structural analogs, or libraries of structural analogs (see, for example, U.S. Pat. Nos. 5,958,792; 5,807,683; 6,004,617; 6,077,954). Such modification can be random or based on rational design (see, for example, Cho et al. 1998 *Pac. Symp. Biocompat.* 305-16; Sun et al. 1998 *J. Comput. Aided Mol. Des.* 12:597-604). For example, libraries of $GABA_A$ receptor antagonists can be prepared by syntheses of combinatorial chemical libraries (see DeWitt et al. 1993 *Proc. Nat. Acad. Sci. USA* 90:6909-13; International Patent Publication WO 94/08051; Baum 1994 *Chem. & Eng. News* 72:20-5; Burbaum et al. 1995 *Proc. Nat. Acad. Sci. USA* 92:6027-31; Baldwin et al. 1995 *J. Am. Chern. Soc.* 117: 5588-89; Nestler et al. 1994 *J. Org. Chem.* 59:4723-24; Borehardt et al. 1994 *J. Am. Chem. Soc.* 116:373-74; Ohlmeyer et al. 1993 *Proc. Nat. Acad. Sci. USA* 90: 10922-26).

6.5 Circadian Cycle Sensitive Administration

Methods for improving cognitive function provided herein can, for example, comprise administering in a circadian cycle sensitive manner a compound that reduces inhibitory neuronal activity, e.g., a $GABA_A$ receptor antagonist, to a subject. Specifically, the compound is administered so that a therapeutic level of the compound or of an active metabolite thereof in the brain of the subject are achieved during the portion of the circadian cycle when the subject sleeps. In some embodiments, the compound is PTZ or another $GABA_A$ receptor antagonist. In certain embodiments, a minimum therapeutic level occurs during sleep. In some embodiments, the peak concentration of the compound occurs or overlaps when the subject sleeps.

During the course of a period of sleep—for instance a night of sleep in a human—the proportion of time spent in the various phases of sleep generally changes. In particular, REM portions of the cycle become longer and non-REM portions of the cycle become shorter during the course of a night of sleep. Thus, chronotherapeutic dosing strategies that target events occurring during a particular phase of sleep can be advantageous. For instance, in certain embodiments, chronotherapeutic dosing strategies that target early portions of the sleep cycle with relatively more slow-wave sleep may be more effective for improving cognitive function for which slow-wave sleep is the time when therapeutic effects occur. In other embodiments, chronotherapeutic dosing strategies that target later portions of the sleep cycle with relatively more REM sleep may be more effective for improving cognitive function for which REM sleep is the time when therapeutic effects occur.

It will be understood that the early, middle and late portions of a subject's sleep cycle will vary depending on length of time the subject typically sleeps, as well as factors such as the type (species), age, health, etc., of the subject.

In some embodiments, the compound that reduces inhibitory neuronal activity, e.g., a $GABA_A$ receptor antagonist, is administered to the subject such that the peak concentration in the subject occurs in an early portion of the subject's sleep cycle. An early portion of a subject's sleep cycle can, for example, be immediately after the subject falls asleep, or within 30 minutes, 1 hour, 2 hours, 3 hours or 4 hours after onset of sleep.

In other embodiments, the compound that reduces inhibitory neuronal activity, e.g., a $GABA_A$ receptor antagonist, is administered to the subject such that the peak concentration in the subject occurs in a middle portion of the subject's sleep cycle. A middle portion of a subject's sleep cycle can, for example, be after 1 hour, after 2 hours, after 3 hours, after 4 hours, after 5 hours or after 6 hours after the subject falls asleep.

In yet other embodiments, the compound that reduces inhibitory neuronal activity, e.g., a $GABA_A$ receptor antagonist, is administered to the subject such that the peak concentration in the subject occurs in a late portion of the subject's sleep cycle. In certain embodiments, a late portion of a subject's sleep cycle can, for example, begin after 3 hours, after 4 hours, after 5 hours, after 6 hours, after 7 hours, after 8 hours or after 9 hours after the onset of sleep.

Normal cognitive function requires sufficient and well-structured sleep. Cognitive impairment due to sleep abnormalities occurs in individuals with neurodevelopmental disorders such as Down syndrome, neurodegenerative disorders such as Alzheimer's disease, various forms of insomnia, sleep apnea, and other pathological conditions. Similarly, reduced memory function unrelated to disease occurs with normal aging, overnight shift work, drug or alcohol use, and other causes of sleep impairment or sleep disruption.

In certain embodiments of the methods provided, the subject is nocturnal and the compound that inhibits neuronal activity, e.g., a $GABA_A$ receptor antagonist, is administered in the morning or during the day. In other embodiments, the subject is diurnal and the $GABA_A$ receptor antagonist is administered in the evening or during the night.

In some embodiments, the compound that reduces inhibitory neuronal activity, e.g., a $GABA_A$ receptor antagonist, is administered in an immediate release formulation that is administered to the subject prior to or during sleep.

In some embodiments, the subject is diurnal and the immediate release formulation is administered in the evening and/or at night. In some embodiments, the immediate release formulation is administered between 6 pm and 8 pm. In some such embodiments, the immediate release formulation is administered between 6 pm and 8 pm, between 8 pm and 10 pm, between 10 pm and midnight, between midnight and 2 am, between 2 am and 4 am, between 4 am and 6 am, or between 6 am and 8 am.

In other embodiments, the subject is nocturnal and the immediate release formulation is administered in the morning and/or during the day. In some embodiments, the immediate release formulation is administered between 6 am and 8 pm. In certain embodiments, the immediate release formulation is administered between 6 am and noon, between 6 am and 8 am, between 8 am and 10 am, between 10 am and noon, between noon and 2 pm, between 2 pm and 4 pm, between 4 pm and 6 pm, or between 6 pm and 8 pm.

In certain embodiments, wherein the compound that reduces inhibitory neuronal activity, e.g., a $GABA_A$ receptor antagonist, is administered in an immediate release formulation, the immediate release formulation is administered once per 24 hour cycle, twice per 24 hour cycle, three times per 24 hour cycle, or four or more times per 24 hour cycle.

In other embodiments, the compound that reduces inhibitory neuronal activity, e.g., a $GABA_A$ receptor antagonist, is used as a delayed release formulation that is administered to the subject prior to or during sleep. Use of a delayed release formulation provides the benefit that the therapeutic concentrations of the compound in the subject can be delayed from the time of administration of the delayed release formulation, enabling administration of the compound prior to the time at which therapeutic efficacy is required (e.g., administration of the compound prior to sleep of the subject to achieve minimum therapeutic levels in the blood or brain during sleep of the subject). In some embodiments, therapeutic concentrations of the compound in the subject's blood or brain are delayed from 30 minutes to 12 hours from the time of administration of the compound. In some embodiments, the therapeutic concentration of the compound in the subject's blood or brain are delayed from 30 to 60 minutes, from 1 hour to 4 hours, or from 4 hours to 8 hours from the time of administration of the delayed release formulation. In some embodiments, the delayed release formulation is administered once per 24 hour cycle, twice per 24 hour cycle, three times per 24 hour cycle, or four or more times per 24 hour cycle.

In some embodiments, the subject is diurnal and the delayed release formulation is administered during the day. In some embodiments, the immediate release formulation is administered between 6 am and 6 pm. In some embodiments, the immediate release formulation is administered between 6 am and 8 am, between 8 am and 10 am, between 10 am and noon, between noon and 2 pm, between 2 pm and 4 pm, or between 4 pm and 6 pm. In some embodiments, the delayed release formulation is administered in the evening and/or at night. In some embodiments, the delayed release formulation is administered 6 pm and midnight or between 6 pm and 8 am. In some embodiments, the immediate release formulation is administered between 6 pm and 8 pm, between 8 pm and 10 pm, between 10 pm and midnight, between midnight and 2 am, between 2 am and 4 am, between 4 am and 6 am, or between 6 am and 8 am.

In some embodiments, the subject is nocturnal and the delayed release formulation is administered during the night. In some embodiments, the immediate release formulation is administered between 6 pm and 8 am. In some embodiments, the immediate release formulation is administered between 6 pm and 8 pm, between 8 pm and 10 pm, between 10 pm and midnight, between midnight and 2 am, between 2 am and 4 am, between 4 am and 6 am, or between 6 am and 8 am. In some embodiments, the delayed release formulation is administered in the morning and/or during the day. In some such embodiments, the delayed release formulation is administered between 8 am and 6 pm. In some such embodiments, the delayed release formulation is administered between 8 am and 10 am, between 10 am and noon, between noon and 2 pm, between 2 pm and 4 pm, or between 4 pm and 6 pm.

In yet other embodiments, the compound that reduces inhibitory neuronal activity, e.g., a $GABA_A$ receptor antagonist, is used as a sustained release formulation that is administered to the subject prior to or during sleep. Use of a sustained release formulation provides the benefit that less frequent dosing is required to achieve the same therapeutic effect as more frequent dosing using an immediate release formulation or a delayed release formulation. In some embodiments, a therapeutically effective dose of the compound in the blood or brain of the subject is maintained from 30 minutes to 12 hours from the time of administration of the sustained release formulation. In certain embodiments, a therapeutically effective dose of the compound in the subject's blood or brain is maintained from 30 to 60 minutes, from 1 hour to 4 hours, or from 4 hours to 8 hours from the time of administration of the sustained release formulation. In some embodiments, a therapeutically effective dose of the compound in the brain of the subject is maintained during sleep of the subject for a period of time greater than 2 hours. In some embodiments, the sustained release formulation is administered once per 24 hour cycle, twice per 24 hour cycle, three times per 24 hour cycle, or four or more times per 24 hour cycle.

In yet other embodiments, the compound that reduces inhibitory neuronal activity, e.g., a $GABA_A$ receptor antagonist, is used as a pulsatile release formulation that is administered to the subject prior to or during sleep. Use of a pulsatile release formulation provides the benefit that repeat dosing can be accomplished with less frequent dosing. This is due to the fact that a pulsatile release formulation can deliver a compound to a specific location within the gastrointestinal tract, optionally together with other additives that may alter the local microenvironment to promote agent stability and uptake of the compound, and can release the compound in pulses without relying on external conditions other than the presence of water. In some embodiments, a therapeutically effective dose of the compound is released in two, three, or four or more pulses over a 12 hour sleep cycle. In some embodiments, the pulsatile release formulation is administered once per 24 hour cycle, twice per 24 hour cycle, three times per 24 hour cycle, or four or more times per 24 hour cycle. Pulsed release technology is described in U.S. Pat. Nos. 4,777,049 and 6,555,136.

In some embodiments of the methods provided, peak concentration of the compound that reduces inhibitory neuronal activity, e.g., a $GABA_A$ receptor antagonist, occurs in the subject while the subject is sleeping, or during a sleep phase of the subject's circadian cycle. In some embodiments, the peak concentration will be that in the subject's blood. In other embodiments, the peak concentration will be that in the subject's brain.

Peak concentration of the $GABA_A$ receptor antagonist can be determined using techniques known in the art appropriate to the compartment (blood or brain) and particular $GABA_A$ receptor antagonist. For example, blood or plasma samples can be taken from the subject to measure the $GABA_A$ receptor antagonist concentration. In certain embodiments, pharmacokinetic parameters (e.g., $C_{max}$ and $T_{max}$) are determined in otherwise healthy subjects from which are derived the pharmacokinetic parameters applicable to the subjects administered in accordance to the methods provided herein.

It will be understood that depending upon a combination of factors such as, for example, the $T_{max}$ of a given $GABA_A$ receptor antagonist, its formulation (which may be for instance, a delayed release formulation or an immediate release formulation, and so forth), among other factors, the $GABA_A$ receptor antagonist is administered to a subject to improve cognition while the subject is awake, for instance, awake although in a sleep phase of her, his or its circadian cycle. In some embodiments, the $GABA_A$ receptor antagonist, is administered prior to sleep, for example, about 3 hr, about 2 hr, about 1 hr, about 30 min, about 20 min, or earlier, prior to onset of sleep.

6.6 Assessing Cognitive Function

Numerous tests or protocols for assessing cognitive function are known in the art. Such tests can, for instance, be employed to assess a cognitive function, or improvement of a cognitive function, in a subject administered with a compound that inhibits neuronal activity, e.g., a $GABA_A$ receptor antagonist, in accordance with the methods provided herein.

In some embodiments, the improvement in cognitive function is determined by measuring a cognitive function in a subject or a population of subjects before and after administration of the dosing regimen. In some embodiments, the improvement in cognitive function or the prevention of reduction in cognitive function is determined by measuring a cognitive function in a subject or a population of subjects to whom are administered the compound as provided herein as compared to measurements made in a subject or a population of subjects to whom the compound is not administered as provided herein.

Assessing improvement in cognitive function or prevention of reduction in cognitive function can be evaluated using any test or protocol known in the art. For instance, the Clinician's Global Impression of Change (CGI/C) has been one of the most commonly used tests to assess overall change in clinical trials. The validity of this type of measure is based on the ability of an experienced clinician to detect a clinically relevant change in a patient's overall clinical state against a trivial change.

Cognitive function in humans can be assessed using any of a number of tests known in the art, including but not limited to tests of IQ, recognition, comprehension, reasoning, remembering, creation of imagery, conation, capacity for judgment, learning, etc., or aspect thereof. See, e.g., Borkowski et al., "Intellectual Assessment and Intellectual Disability" in *Handbook of Intellectual and Developmental Disabilities* (eds. Jacobson et al. Springer Science+Business Media, LLC, New York, 2007), Chapter 14, pages 261-278. Assessment tests include, for example, the Diagnostic Adaptive Behavior Scale (DABS), the Wechsler Adult Intelligence Scale (WAIS) including it revisions, the WAIS-R and WAIS-III, the Mini-Mental State Examination (MMSE) or "Folstein" test, the Blessed Information-Memory-Concentration Test (BIMC), the Fuld Object Memory Evaluation (FOME), the California Verbal Learning Test (CVLT) and revised version (CVLT-II), the DAME battery, and the like.

Likewise, learning and memory in animals can be assessed using any of a variety of standardized tests. Examples include analysis of sustained and non-sustained attention and impulsivity, e.g. acquisition inhibitory avoidance responding, 5-choice serial reaction time testing in rodents, and a distractor version of a Delayed Match to Sample test in monkeys. Analysis of social and working memory may include but is not limited to tasks involving a social recognition model, spatial working memory using a water maze in rats, and spontaneous alternation Y mazes. Analysis of spatial reference memory may include but is not limited to mazes, e.g. water maze with a hidden platform, 2-choice visual discrimination water maze, and "dry land" Barnes circular maze, wherein different configurations of the water maze can be used to measure different forms of learning and different brain systems. Analysis of cued and contextual learning and memory may include but is not limited to the conditioned fear test, in which freezing behavior in response to discrete conditioned stimuli such as tones or lights is used as a measure of learning. A passive avoidance model is useful in assessing recall.

6.7 Dosages, Dosing Regimens and Formulations

In one aspect, dosing regimens and formations useful for improving cognition in a subject are provided as described herein.

The dosage and dosing regimen for the administration of the compound that reduces inhibitory neuronal activity, e.g., a $GABA_A$ receptor antagonist, as provided herein is selected by one of ordinary skill in the art, in view of a variety of factors, including, without limitation, age, weight, sex, and medical condition of the subject, the severity of the condition to be treated, the route of administration, the level of metabolic and excretory function of the subject, the dosage form employed, the particular compound and salt thereof employed, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the compound or formulation thereof.

The dosage and dosing regimen for the administration of the compound that reduces inhibitory neuronal activity, e.g., a $GABA_A$ receptor antagonist, as provided herein is also influenced by toxicity in relation to therapeutic efficacy. Toxicity and therapeutic efficacy can be determined according to standard pharmaceutical procedures in cell cultures and/or experimental animals, including, for example, determining the LD50 (the dose lethal to 50% of the population, or, alternatively, for the methods provided herein, the dose that kindle seizures in 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are generally preferred.

The effective dose of the compound that reduces inhibitory neuronal activity, e.g., a $GABA_A$ receptor antagonist, can, for example, be less than 15 mg/kg of subject body mass, less than 10 mg/kg, less than 5 mg/kg, less than 3 mg/kg, less than 1 mg/kg, less than 0.3 mg/kg, less than 0.1 mg/kg, less than 0.05 mg/kg, less than 0.025 mg/kg, or less than 0.01 mg/kg. Doses of the compound that reduces inhibitory neuronal activity, e.g., $GABA_A$ antagonist, administered to a subject as provided in the methods herein can, for example, be between about 0.001 mg/kg to about 15 mg/kg. In certain embodiments, the effective dose is in the range of, for example, 0.005 mg/kg to 10 mg/kg, from 0.01 mg/kg to 2 mg/kg, or from 0.05 mg/kg to 0.5 mg/kg. In various embodiments, an effective dose is less than 1 g, less than 500 mg, less than 250 mg, less than 100 mg, less than 50 mg, less than 25 mg, less than 10 mg, less than 5 mg, less than 1 mg, less than 0.5 mg, or less than 0.25 mg per dose, which dose may be administered once, twice, three times, or four or more times per day. In certain embodiments, an effective dose can be in the range of, for example, from 0.1 mg to 1.25 g, from 1 mg to 250 mg, or from 2.5 mg to 70 mg per dose. The daily dose can be in the range of, for example, from 0.5 mg to 5 g, from 1 mg to 1 g, or from 3 mg to 300 mg. An effective dose of bilobalide or ginkgolide B may range from at least about 0.1 mg/kg, at least about 0.2 mg/kg, at least about 0.5 mg/kg, at least about 1 mg/kg to not more than about 5 mg/kg or not more than about 2.5 mg/kg. Exemplary doses of PTZ can be, for instance, from 0.001 mg/kg to 15 mg/kg, from 0.005 mg/kg to 12 mg/kg, from 0.1 mg/kg to 10 mg/kg, from 0.2 mg/kg to 5 mg/kg, from 0.15 mg/kg to 3 mg/kg, from 0.25 mg/kg to 1 mg/kg, from 0.5 mg/kg to 7 mg/kg, from 0.001 mg/kg to 0.5 mg/kg or from 1 mg/kg to 5 mg/kg per subject body mass.

In certain embodiments, the dose of $GABA_A$ receptor antagonist administered is less than a kindling dose applicable to the subject being administered with the $GABA_A$ receptor antagonist. In some embodiments, the dosage is less than about 0.5-fold the kindling dose, less than about 0.3-fold the kindling dose, less than about 0.1-fold the kindling dose, less than about 0.05-fold the kindling dose, less than about 0.01-fold the kindling dose, or about less than about 0.005-fold the kindling dose.

The compound that reduces inhibitory neuronal activity, e.g., a $GABA_A$ receptor antagonist, may be administered in a single daily dose, or the total daily dose may be administered in divided doses, two, three, or more times per day. In some embodiments, the dosing regimen is maintained for at least about two days, at least about one week, at least about two weeks, at least about three weeks, at least about one month, or longer. In some embodiments, an intermittent dosing regimen is used, i.e., once a month, once every other week, once every other day, once per week, twice per week, and the like. In some embodiments, the compound is administered at least once daily for at least five consecutive days.

In some embodiments, an effective dose of the compound that reduces inhibitory neuronal activity, e.g., a $GABA_A$ receptor antagonist, will transiently reduce the chloride influx at $GABA_A$ receptors in the central nervous system, for example for a period of at least about 1 minute, at least about 5 minutes, at least about 30 minutes, at least about 1 hours, or more, usually not more than about 4 hours, not more than about 3 hours, or not more than about 2 hours. However, there may also be embodiments where the effective dose provides for a longer lasting reduction of chloride ion influx at $GABA_A$ receptors in the central nervous system, for example for at least about 5 hours, at least about 6 hours, at least about 7 hours, at least about 8 hours, at least about 9 hours, at least about 10 hours, at least about 11 hours, at least about 12 hours, or longer. Such embodiments may provide for a more continuous activity profile, for example by using a continuous pump or by administering an effective dose more than once a day (e.g., twice, three times, four times, and more per day).

The compound that reduces inhibitory neuronal activity, e.g., a $GABA_A$ receptor antagonist, is administered to the subject as a pharmaceutical composition that includes an effective amount of the compound in a pharmaceutically acceptable vehicle. It can be incorporated into a variety of formulations for therapeutic administration by combination with appropriate pharmaceutically acceptable carriers or diluents, and may be formulated into preparations in solid, semi-solid, liquid, or gaseous forms, such as tablets, capsules, powders, granules, ointments, solutions, suppositories, injections, inhalants, gels, microspheres, and aerosols.

In some embodiments, the compound that reduces inhibitory neuronal activity, e.g., a $GABA_A$ receptor antagonist, is formulated as a delayed release formulation. Suitable pharmaceutical excipients and unit dose architecture for delayed release formulations may include those described in U.S. Pat. Nos. 3,062,720 and 3,247,066. Delayed release formulations can be formulated in tablets that can be coated using known methods to achieve delayed disintegration in the gastrointestinal tract of a human. By way of example, a material such as glyceryl monostearate or glyceryl distearate can be used to coat tablets. Further by way of example, tablets can be coated using methods described in U.S. Pat. Nos. 4,256,108; 4,160,452; and 4,265,874 to form osmotically-controlled release tablets. Oral compositions that specifically release orally-administered agents in the small or large intestines of a human patient can be made using known technology. For example, formulations for delivery to the gastrointestinal system, including the colon, include enteric coated systems, based, e.g., on methacrylate copolymers such as poly(methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon. See Hardy et al. 1987 *Aliment Pharmacol. Ther.* 1:273-80. Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend & Chang 1984 *J. Med. Chem.* 27:261-6) and a variety of naturally available and modified polysaccharides (see PCT application PCT/GB89/00581) can be used in such formulations.

In other embodiments, the compound that reduces inhibitory neuronal activity, e.g., a $GABA_A$ receptor antagonist, is formulated as a sustained release formulation. Suitable pharmaceutical excipients and unit dose architecture for sustained release formulations include those described in U.S. Pat. Nos. 3,062,720 and 3,247,066. The compound that reduces inhibitory neuronal activity either in its free form or as a salt can be combined with a polymer such as polylactic-glycoloic acid (PLGA), poly-(I)-lactic-glycolic-tartaric acid (P(I)LGT) (WO 01/12233), polyglycolic acid (U.S. Pat. No. 3,773,919), polylactic acid (U.S. Pat. No. 4,767,628), poly (ε-caprolactone) and poly(alkylene oxide) (U.S. 20030068384) to create a sustained release formulation. Such formulations can be used in implants that release an agent over a period of several hours, a day, a few days, a few weeks, or several months depending on the polymer, the particle size of the polymer, and the size of the implant (see, e.g., U.S. Pat. No. 6,620,422). Other sustained release formulations are described in EP 0 467 389 A2, WO 93/241150, U.S. Pat. No. 5,612,052, WO 97/40085, WO 03/075887, WO 01/01964A2, U.S. Pat. No. 5,922,356, WO 94/155587, WO 02/074247A2, WO 98/25642, U.S. Pat. Nos. 5,968,895, 6,180,608, U.S. 20030171296, U.S. 20020176841, U.S. Pat. Nos. 5,672,659, 5,893,985, 5,134,122, 5,192,741, 5,192,741, 4,668,506, 4,713,244, 5,445,832 4,931,279, 5,980,945, WO 02/058672, WO 9726015, WO 97/04744, and. US20020019446. In such sustained release formulations microparticles of drug are combined with microparticles of polymer. One or more sustained release implants can be placed in the large intestine, the small intestine, or both. U.S. Pat. No. 6,011,011 and WO 94/06452 describe a sustained release formulation providing either polyethylene glycols (where PEG 300 and PEG 400 are most preferred) or triacetin. WO 03/053401 describes a formulation that may both enhance bioavailability and provide controlled release of the agent within the GI tract. Additional sustained release formulations are described in WO 02/38129, EP 326 151, U.S. Pat. No. 5,236,704, WO 02/30398, WO 98/13029; U.S. 20030064105, U.S. 20030138488A1, U.S. 20030216307A1,U.S. Pat. No. 6,667,060, WO 01/49249, WO 01/49311, WO 01/49249, WO 01/49311, and U.S. Pat. No. 5,877,224.

In certain embodiments, a delayed release formulation is such that the peak concentration of the compound that reduces inhibitory neuronal activity, e.g., a $GABA_A$ receptor antagonist, occurs in the subject by 30 minutes to 8 hours from the time of administration. In certain embodiments, the delayed release formulation delays the peak in the subject's blood or in the subject's brain by 30 minutes to 1 hour, by 1 hour to 4 hours, or by 4 hours to 8 hours, from the time of administration.

In certain embodiments, a sustained release formulation is such that a peak concentration of the compound that reduces inhibitory neuronal activity, e.g., a $GABA_A$ receptor antagonist, is maintained in the subject for 30 minutes to 8 hours after being administered to the subject. In certain embodiments, the sustained release formulation maintains a peak in the subject's blood or in the subject's brain for 30 minutes to 60 minutes, for 1 hour to 4 hours, or for 4 hours to 8 hours, after administration to the subject.

Pharmaceutical compositions can include, depending on the formulation desired, pharmaceutically-acceptable, non-toxic carriers of diluents, which are defined as vehicles commonly used to formulate pharmaceutical compositions for animal or human administration. The diluent is selected so as not to affect the biological activity of the combination. Examples of such diluents are distilled water, buffered water, physiological saline, PBS, Ringer's solution, dextrose solution, and Hank's solution. In addition, the pharmaceutical composition or formulation can include other carriers, adjuvants, or non-toxic, nontherapeutic, nonimmunogenic stabilizers, excipients, and the like. The compositions can also include additional substances to approximate physiological conditions, such as pH adjusting and buffering agents, toxicity adjusting agents, wetting agents, and detergents. The composition can also include any of a variety of stabilizing agents, such as an antioxidant for example. Tablet formulations can comprise a sweetening agent, a flavoring agent, a coloring agent, a preservative, or some combination of these to provide a pharmaceutically elegant and palatable preparation.

Further guidance regarding formulations that are suitable for various types of administration can be found in *Remington's Pharmaceutical Sciences*, Mace Publishing 20 Company, Philadelphia, Pa., 17th ed. (1985).

For oral administration, the compound that reduces inhibitory neuronal activity can be administered in solid dosage forms, such as capsules, tablets, and powders, or in liquid dosage forms, such as elixirs, syrups, and suspensions. The compound can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

6.8 Administration

The compound that reduces inhibitory neuronal activity, e.g., a $GABA_A$ receptor antagonist, may be administered to the subject using any convenient means capable of resulting in the desired improvement on cognitive function. Routes of administration include but are not limited to oral, rectal, parenteral, intravenous, intracranial, intraperitoneal, intradermal, transdermal, intrathecal, intranasal, intracheal, intracapillary, subcutaneous, subdermal, topical, intramuscular, injection into the cerebrospinal fluid, injection into the intracavity, or injection directly into the brain. Oral administration can include, for instance, buccal, lingual, or sublingual administration. The compound that reduces inhibitory neuronal activity may be systemic after administration or may be localized by the use of regional administration, intramural administration, or use of an implant that acts to retain the active dose at the site of implantation. For a brief review of methods for drug delivery see Langer 1990 *Science* 249:1527-1533.

In some embodiments, the compound that reduces inhibitory neuronal activity can cross the blood brain barrier (BBB) to be bioactive in the central nervous system after oral or parenteral administration. In other embodiments, the compound that reduces inhibitory neuronal activity cannot cross the blood brain barrier. In such embodiments, one strategy for drug delivery through the BBB entails disruption of the BBB, either by osmotic means such as mannitol or leukotrienes, or biochemically by the use of vasoactive substances such as bradykinin. The potential for using BBB opening to target specific agents is also an option. A BBB disrupting agent can be co-administered with the therapeutic compositions of the invention when the compositions are administered by intravascular injection. Other strategies to go through the BBB may entail the use of endogenous transport systems, including carrier-mediated transporters such as glucose and amino acid carriers, receptor-mediated transcytosis for insulin or transferrin, and active efflux transporters such as p-glycoprotein. Active transport moieties may also be conjugated to the therapeutic or imaging compounds for use in the invention to facilitate transport across the epithelial wall of the blood vessel. Alternatively, drug delivery behind the BBB can be by intrathecal delivery of therapeutics or imaging agents directly to the cranium, as through an Ommaya reservoir (Balis et al. 1989 *Am J. Pediatr. Hematol. Oncol.* 11:74-6).

7. EXAMPLES

This example shows that administration of a $GABA_A$ receptor antagonist during sleep improves cognitive function.

In this case, the effect of the noncompetitive $GABA_A$ receptor antagonist pentylenetetrazole (PTZ) on cognitive function in the Ts65Dn mouse model of Down syndrome was assessed with the Novel Object Recognition (NOR) task.

The NOR task is based on the established finding that mice preferentially explore novel objects relative to remembered objects. The test consists of a training session and a testing session. During the training session, a mouse is allowed 15 minutes to explore freely a training chamber that contains two objects. The amount of time the mouse uses to explore each object is quantified using video monitoring. The mouse is removed from the training session for 24 hours, during which time one of the objects in the training chamber is replaced with a novel object. The mouse is returned to the training chamber for the testing session, during which video monitoring is again used to quantify the amount of time the mouse uses to explore each object.

Ts65Dn mice and wild-type (2N) controls were maintained on a 12:12 light:dark (LD) cycle. At three months of age, their NOR task performance was determined. The animals then received daily intraperitoneal (IP) injections of pentylenetetrazole (PTZ; 0.3 mg/kg) for two weeks ("treatment"). A control group received vehicle control (saline; NaCl) only for the same duration. The IP injections occurred near the middle of the light phase or during the dark phase of a LD cycle. Two weeks after treatment end, the NOR task performance of all mice was again determined. All NOR tasks were performed during the light phase of a LD cycle.

Figure 1:
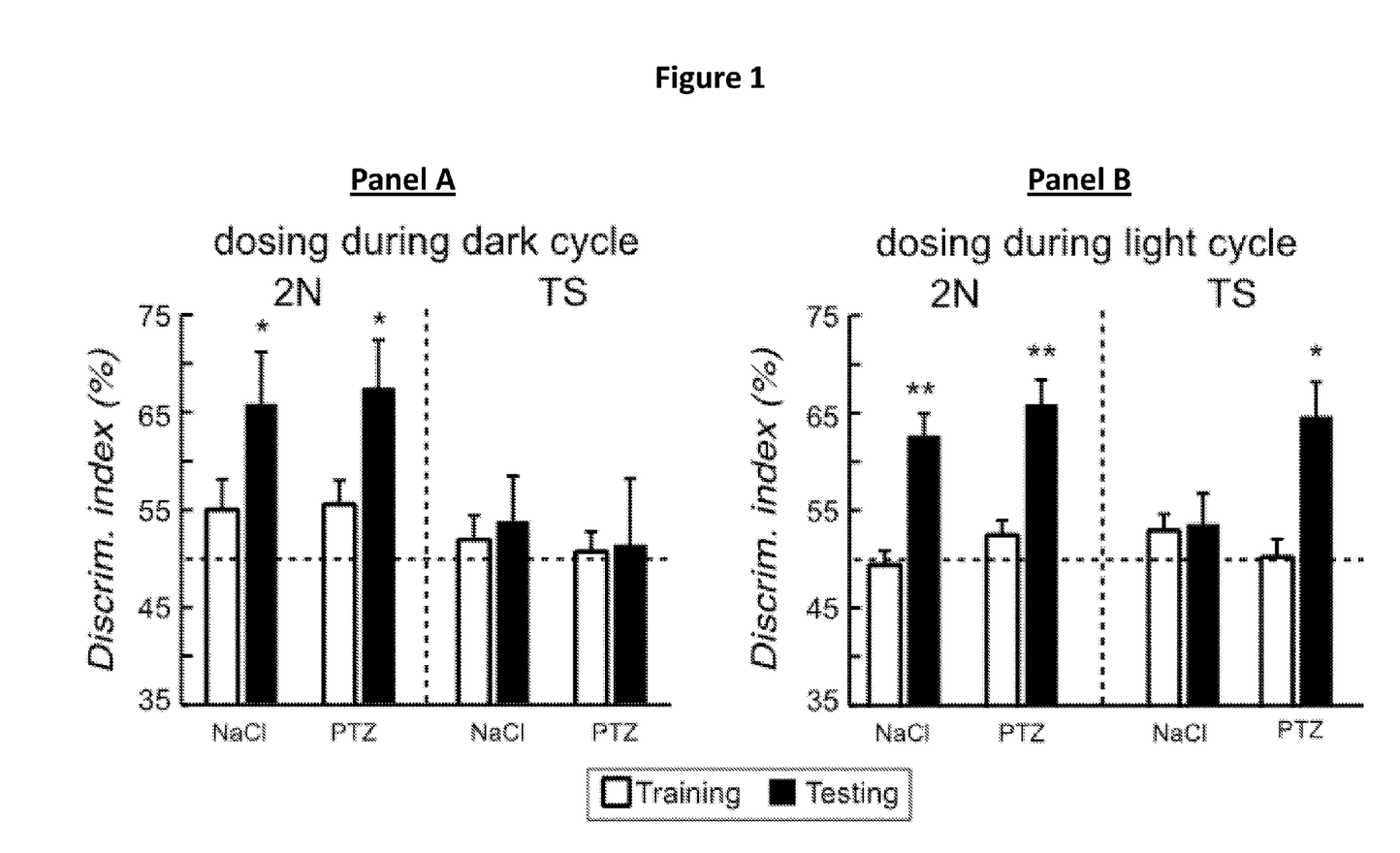
FIG. 1 contrasts dosing of pentylenetetrazole (PTZ) versus vehicle (NaCl) in normal mice (2N) versus Ts65Dn mice during the dark cycle (Panel A) and during the light cycle (Panel B).

For each cohort, the relative learning index values were compared to 50%, the level expected for exploration of two novel (not remembered) objects, with a one-sample t-test. Single and double asterisks in FIG. 1 indicate $p<0.05$ and $p<0.01$, respectively. Data represented in FIG. 1 are mean±SEM (n=7 to 9 per group). The results depicted in FIG. 1 are similar to results observed in a preliminary study following a protocol like that described above, which results were shown in FIGS. 1 and 2 of U.S. Provisional Application No. 61/424,168, filed Dec. 17, 2010, and which are incorporated herein.

As shown in panel B, left side, of FIG. 1, wild-type (2N) mice treated with 0.3 mg/kg PTZ ("PTZ") or saline ("NaCl") spent about an equal amount of time on each object during the training session, but more time on the new object during the testing session. In comparison, as shown in panel B, right side, of FIG. 1 and in Panel A, right side, FIG. 1, Ts65Dn mice treated with saline ("NaCl") during the light or dark phase of their LD cycle spent an approximately equal amount of time of the testing session exploring both the novel and previously presented objects, showing a failure by these mice to recall the previously presented object. However, Ts65Dn mice treated with PTZ during the light phase of their LD cycle (when the mice were asleep) spent a significantly larger proportion of time of the testing session exploring the novel object, indicating that learning and memory function were improved by the PTZ treatment, as can be seen in Panel B, right side, of FIG. 1. As shown in Panel A, right side, of FIG. 1, while Ts65Dn mice treated with PTZ during the dark phase of their LD cycle (when the mice were awake) had some improvement relative to the saline-injected controls, these mice did not show the same degree of improvement on their NOR task performance as compared to the Ts65Dn mice treated with PTZ during the light phase, as shown in Panel B, right side, of FIG. 1.

These results demonstrate that improvement in a cognitive function in a subject with administration of a $GABA_A$ receptor antagonist such as PTZ is dependent upon when the $GABA_A$ receptor antagonist is administered to the subject. In particular, that improvement can be observed when the $GABA_A$ receptor antagonist is administered during a sleep cycle.

The examples set forth herein are provided to give those of ordinary skill in the art with a complete disclosure and description of how to make and use the embodiments, and are not intended to limit the scope of the disclosure. Modifications of the above-described modes for carrying out the disclosure that are obvious to persons of skill in the area intended to be within the scope of the following claims.

All publications, patents, and patent applications cited in this specification are incorporated herein by reference as if each such publication, patent, or patent application were specifically and individually indicated to be incorporated herein by reference.

What is claimed is:

1. A method for improving a cognitive function in a human subject with Down syndrome comprising administering to the human subject a therapeutically effective dose of a $GABA_A$ receptor chloride ionophore blocker, wherein the $GABA_A$ receptor chloride ionophore blocker is pentylenetetrazole, picrotoxin or bilobalide, in a circadian cycle sensitive manner so that peak concentration of the $GABA_A$ receptor chloride ionophore blocker in the human subject occurs when the human subject is asleep, wherein the administering is effective to achieve improvement in the Down syndrome.

2. The method of claim 1, wherein the $GABA_A$ receptor chloride ionophore blocker is pentylenetetrazole.

3. The method of claim 1, wherein the $GABA_A$ receptor chloride ionophore blocker is administered at least once daily for at least five consecutive days.

4. The method of claim 1, wherein the $GABA_A$ receptor chloride ionophore blocker is administered only once a day.

5. The method of claim 1, wherein the $GABA_A$ receptor chloride ionophore blocker is administered no more than two hours before the subject goes to sleep.

6. The method of claim 1, wherein the $GABA_A$ receptor chloride ionophore blocker is administered at a dose of 0.001 to 15 mg/kg body weight of the subject.

7. The method of claim 1, wherein the $GABA_A$ receptor chloride ionophore blocker is administered in a delayed release formulation.

8. The method of claim 7, wherein the delayed release formulation delays the peak concentration of the $GABA_A$ receptor chloride ionophore blocker in brain by 30 min to 8 hours from the time of administration.

9. The method of claim 1, wherein the $GABA_A$ receptor chloride ionophore blocker is administered in a sustained release formulation.

10. The method of claim 9, wherein the sustained release formulation maintains a therapeutically effective dose of the $GABA_A$ receptor chloride ionophore blocker for 30 min to 8 hours after administration.

11. The method of claim 1, wherein the peak concentration of the $GABA_A$ receptor chloride ionophore blocker in the subject occurs in the middle or late portion of the subject's sleep cycle.

* * * * *